United States Patent [19]

Lombardino

[11] 4,289,879
[45] Sep. 15, 1981

[54] SYNTHETIC METHOD AND INTERMEDIATE FOR PIROXICAM

[75] Inventor: Joseph G. Lombardino, Niantic, Conn.

[73] Assignee: Pfizer Inc., New York, N.Y.

[21] Appl. No.: 191,716

[22] Filed: Sep. 29, 1980

[51] Int. Cl.³ .......................................... C07D 279/02
[52] U.S. Cl. ..................................................... 544/49
[58] Field of Search ......................................... 544/49

[56] References Cited

U.S. PATENT DOCUMENTS

| | | | |
|---|---|---|---|
| 3,501,466 | 3/1970 | Rasmussen | 544/49 |
| 3,591,584 | 7/1971 | Lombardino | 544/49 |
| 3,816,628 | 6/1974 | Zinnes et al. | 544/49 |

*Primary Examiner*—John M. Ford
*Attorney, Agent, or Firm*—Connolly and Hutz

[57] ABSTRACT

2-Methoxyethyl 4-hydroxy-2-methyl-2H-1,2-benzothiazine-3-carboxylate 1,1-dioxide is an advantageous ester precursor for piroxicam (4-hydroxy-2-methyl-N-2-pyridyl-2H-1,2-benzothiazine-3-carboxamide 1,1-dioxide), an antiinflammatory agent established in medical practice.

4 Claims, No Drawings

SYNTHETIC METHOD AND INTERMEDIATE FOR PIROXICAM

BACKGROUND OF THE INVENTION

This invention is concerned with 2-methoxyethyl 4-hydroxy-2-methyl-2H-1,2-benzothiazine-3-carboxylate 1,1-dioxide,

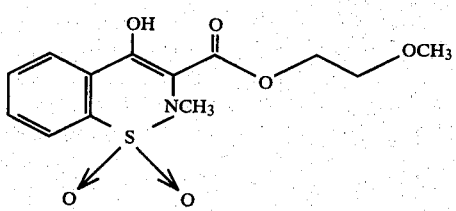    (I)

an ester having special value in the synthesis of piroxicam (4-hydroxy-2-methyl-N-2-pyridyl-2H-1,2-benzothiazine-3-carboxamide 1,1-dioxide)

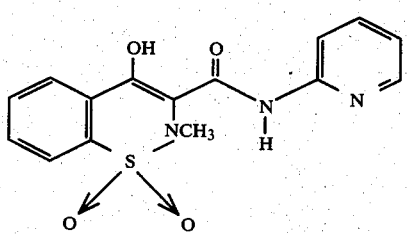    (II)

an antiinflammatory agent of established value in the medicinal art. It will be noted that in past practice, the acyl radical of compounds of this type has been sometimes written as

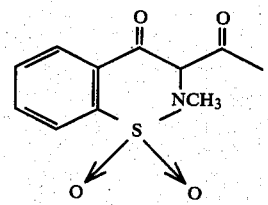

and such compounds alternatively named as 3,4-dihydro-2-methyl-4-oxo-2H-1,2-benzothiazine 1,1-dioxide derivatives. Those skilled in the art will understand that these are equivalent tautomeric forms of the same compound. The present invention is intended to encompass both tautomeric forms while writing only one of them as a matter of convenience.

Piroxicam was originally disclosed by Lombardino (U.S. Pat. No. 3,591,584). One of the processes for the synthesis of piroxicam disclosed therein is to react a 3-carboxylic acid ester with 2-aminopyridine. More specifically, the ester is disclosed as a ($C_1$–$C_{12}$)alkyl ester or phenyl($C_1$–$C_3$)alkyl ester. The specific ester described is the methyl ester, viz.

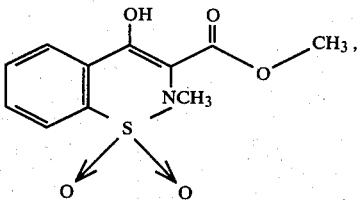    (III)

[See also Lombardino et al., J. Med. Chem. 14, pp. 1171–1175 (1971)]. A disadvantage in this otherwise useful process for piroxicam lies in the variable formation of quantities of a highly colored byproduct. This highly colored byproduct, which is removed only by multiple recrystallizations with major product loss, lends an unacceptable, strong yellow color to the piroxicam bulk product, even when present at very low levels (e.g., 0.5–1%). This byproduct has been isolated and determined to have the following structure:

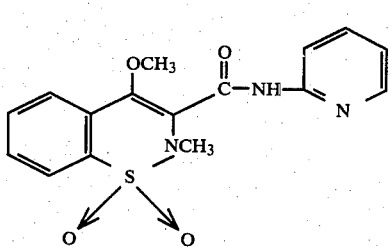    (IV)

It has been shown that (IV) is actually formed as a byproduct in the reaction, rather than being derived from a contaminant in the precursor. How this compound is actually formed in the reaction mixture is not fully understood, although methods which are directed to rapid removal of the methanol byproduct as it is formed in the reaction appear to reduce the incidence of piroxicam batches having unacceptable color. However, these methods are of uncertain dependability and a goal has been to find an ester which is readily available by synthesis and which does not give rise to an ether such as (IV) as a troublesome byproduct during conversion to piroxicam.

Alternative syntheses of piroxicam which have been disclosed in the literature include reaction of 3,4-dihydro-2-methyl-4-oxo-2H-1,2-benzothiazine 1,1-dioxide with 2-pyridyl isocyanate (Lombardino, U.S. Pat. No. 3,591,584), transamidation of 4-hydroxy-2-methyl-2H-1,2-benzothiazine-3-carboxanilides with 2-aminopyridine (Lombardino, U.S. Pat. No. 3,891,637), cyclization of

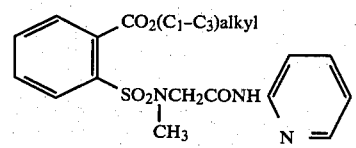

(Lombardino, U.S. Pat. No. 3,853,862), coupling of a 4-($C_1$–$C_3$)alkoxy-2-methyl-2H-1,2-benzothiazine-3-carboxylic acid 1,1-dioxide with 2-aminopyridine followed by hydrolysis of the enolic ether linkage (Lombardino U.S. Pat. No. 3,892,740), coupling of 4-hydroxy-2-methyl-2H-1,2-benzothiazine-3-carboxylic acid, via the acid chloride, with 2-aminopyridine (Hammen, U.S. Pat.

No. 4,100,347) and methylation of 4-hydroxy-N-2-pyridyl-2H-1,2-benzothiazine-3-carboxamide (Canada Pat. No. 1,069,894).

Another ester related to the methoxyethyl ester of the present invention which has been specifically described in the literature is ethyl 4-hydroxy-2-methyl-2H-1,2-benzothiazine-3-carboxylate 1,1-dioxide (Rasmussen, U.S. Pat. No. 3,501,466; see also Zinnes et al., U.S. Pat. No. 3,816,628).

SUMMARY OF THE INVENTION

The 2-methoxyethyl ester (I) has been synthesized. In the known process of converting a corresponding 3-carboxylic acid ester to piroxicam, this ester has been substituted for the prior art methyl ester (III). Use of the novel ester (I) has the surprising advantage that the piroxicam so produced contains no detectable level of the expected, highly-colored ether byproduct [4-(2-methoxyethoxy)-2-methyl-N-2-pyridyl-2H-1,2-benzothiazine-3-carboxamide], of the formula

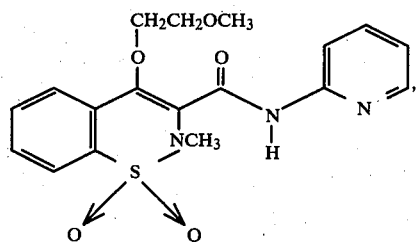
(V)

analogous to the ether (IV).

DETAILED DESCRIPTION OF THE INVENTION

The required 2-methoxyethyl ester (I) is readily prepared from saccharin-2-acetate ester [2-methoxyethyl-3-oxo-2H-1,2-benzisothiazoline-2-acetate 1,1-dioxide, formula (VI)] by the following sequence of reactions

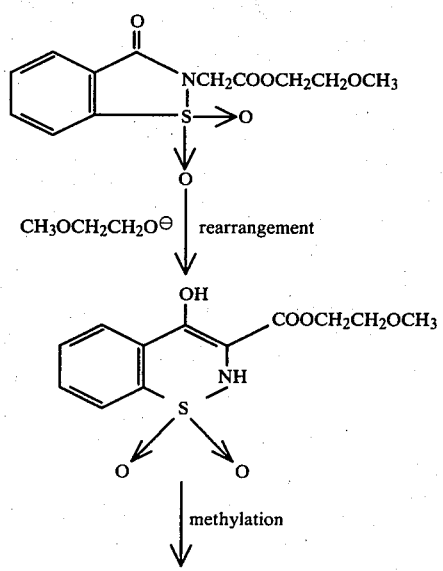

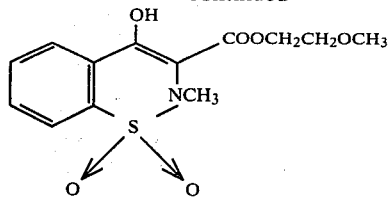
(I)

The rearrangement is carried out by treating the intermediate saccharin-2-acetic acid ester with an alkoxide, preferably a 2-methoxyethoxide such as sodium 2-methoxyethoxide in order to avoid the complication of transesterification, in a polar organic solvent such as dimethyl sulfoxide or dimethylformamide. Methylation is accomplished by a methylating agent, such as dimethyl sulfate or a methyl halide, conveniently methyl iodide, in a reaction-inert solvent such as a lower ketone, a lower alkanol, formamide, dimethylformamide or dimethylsulfoxide.

The saccharin-2-acetic acid ester required as starting material in the above sequence is prepared from saccharin and 2-methoxyethyl chloroacetate in analogy to the method for preparation of the corresponding methyl ester [Chemische Berichte 30, p. 1267 (1897)], or, less directly, by hydrolysis of said methyl ester to the corresponding saccharin acetic acid and coupling, such as via the acid chloride, with 2-methoxyethanol.

The reaction of the methoxy ester (I) with 2-aminopyridine to produce piroxicam,

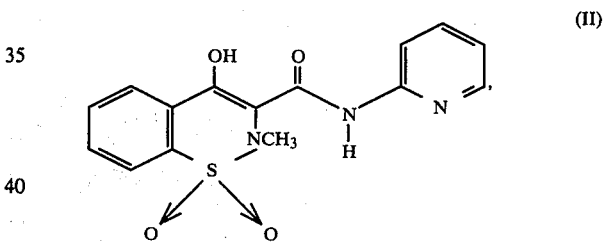
(II)

is generally conducted by mixing the two components together in a reaction-inert solvent system at or near room temperature, and then heating the resultant system at 115°–117° C. for a period of about one-half to several hours. Although it is only necessary that these two reactants be present in substantially equimolar amounts in order to effect the reaction, a slight excess of one or the other (and preferably the more readily available amine base reagent) is not harmful in this respect and may even serve to shift the ammonolysis reaction to completion. Preferred reaction-inert organic solvents for use in the ammonolysis reaction include such lower N,N-dialkylalkanamides as dimethylformamide, dimethylacetamide and the like, as well as such aromatic hydrocarbons solvents as benzene, toluene, xylene and so forth. In any event, it is found most helpful and usually suitable to distill off the volatile alcohol byproduct as it is formed in the reaction and thereby shift the ammonolysis equilibrium to completion in this manner. In the present instance, the most highly preferred solvent is xylene, since byproduct 2-methoxyethanol is efficiently removed as a lower boiling azeotrope. The volume of xylene can be maintained by the addition of more xylene during distillation. After removal of the alcohol and completion of the reaction, the resulting piroxicam is conveniently recovered by cooling and simple filtration of the crystallized product. If desired, the piroxicam is recrystallized from dimethylacetamide/acetone/water.

The present invention is illustrated by the following examples. However, it should be understood that the invention is not limited to the specific details of these examples.

EXAMPLE 1

4-(2-Methoxyethoxy)-2-methyl-N-2-pyridyl-2H-1,2-benzothiazine-3-carboxamide 1,1-Dioxide

[$O^4$-(2-methoxyethyl)piroxicam] (V)

In a flame dried flask maintained under a dry nitrogen atmosphere, piroxicam (1.814 g., 5.47 mmoles) was dissolved in 13 ml. of dry dimethylformamide. Sodium hydride (0.131 g., 5.47 mmoles) was added slowly in portions and the resulting mixture heated at 40°–45° C. for about 3 hours, until such time as the sodium hydride had completely reacted. 2-Methoxyethyl chloride (1.0 ml., 0.94 mmoles) and sodium iodide (0.821 g., 5.47 mmoles) were then added and the reaction then heated at 89° C. for 51 hours. The cooled reaction mixture was diluted with about 50 g. of ice and extracted with five 10 ml. portions of methylene chloride. The organic extracts were combined, back-washed with seven 15 ml. portions of water, washed once with brine, dried over anhydrous magnesium sulfate, filtered and evaporated to an oil (1.44 g.). The oil was triturated with ether, yielding solids (0.84 g.), which were recrystallized from acetonitrile (yielding 0.57 g.). Recrystallized product (0.45 g.) was chromatographed on silica gel (13.5 g.), eluting with 2:3:6 methanol:cyclohexane:ethyl acetate and monitoring by TLC (same eluant) with phosphomolybdic spray. Early cuts, containing clean product, were combined, evaporated in vacuo to solids. The solids were chased with carbon tetrachloride and dried under high vacuum yielding $O^4$-(2-methoxyethyl)piroxicam. [0.31 g.; m.p. 155°–157° C.; Rf 0.5 (2:3:6 methanol:cyclohexane:ethyl acetate); Rf 0.4 (10:4:3 xylene:methanol:water); pnmr/$CDCl_3$/delta 3.15 (s, 3H), 3.35 (s, 3H), 3.68 (m, 2H), 4.23 (m, 2H), 7.2 (m, 1H), 7.9 (m, 5H), 8.9 (m, 2H), 10.2 (broad s, 1H)].

EXAMPLE 2

2-Methoxyethyl 2-Chloroacetate

Maintaining a temperature of −5° to 5° C., 2-chloroacetyl chloride (11.2 g., 0.10 mole) in 15 ml. of methylene chloride was added dropwise over 1 hour to a cold solution of pyridine (8.0 g., 0.11 mole) and 2-methoxyethanol (7.6 g., 0.10 moles) in 35 ml. of methylene chloride. The reaction mixture was stirred for a further 1 hour at 0° C., warmed to room temperature and extracted with two 50 ml. portions of water. The two aqueous extracts were combined and back-washed with 50 ml. of chloroform. The original organic layer and chloroform back-wash were combined and washed with 50 ml. of 5% copper sulfate. The 5% copper sulfate wash was backwashed with 25 ml. of chloroform and recombined with the organic phase. Finally, the organic phase was washed with 50 ml. of brine, treated with activated carbon and anhydrous magnesium sulfate, filtered, concentrated to an oil and distilled to yield 2-methoxyethyl 2-chloroacetate (14.1 g.; b.p. 80°–82° C.).

EXAMPLE 3

2-Methoxyethyl 3-Oxo-2H-1,2-benzisothiazoline-2-acetate 1,1-Dioxide (2-Methoxyethyl Saccharin-2-acetate) (VI)

Sodium saccharin (18 g., 0.088 mole) and 2-methoxyethyl 2-chloroacetate (13.4 g., 0.088 mole) were combined in 40 ml. of dimethylformamide and heated at 120° C. for 4 hours. The reaction mixture was cooled to 25° C., poured into 100 ml. of water, granulated at 5°–10° C. for 0.5 hour, filtered with water wash and air dried to yield 2-methoxyethyl saccharin-2-acetate [23.2 g., 90%; m.p. 91°–92° C.; m/e 299; ir(KBr) 2985 $cm^{-1}$].

EXAMPLE 4

2-Methoxyethyl 4-Hydroxy-2H-1,2-benzothiazine-3-carboxamide 1,1-dioxide

Under a dry nitrogen atmosphere, 2-methoxyethanol (72.9 ml., 0.924 mole) was charged to a stirred, flame-dried flask. Sodium spheres (10.6 g., 0.463 mole; pentane washed and slightly flattened with tweezers) were added portionwise over 2 hours, keeping the temperature of the reaction mixture in the range of 25°–45° C. After an additional 1 hour of stirring, a further 10 ml. of 2-methoxyethanol was added and the reaction mixture warmed to 57° C. On slight cooling the reaction mixture solidified. The reaction mixture was thinned with 75 ml. of dry dimethylsulfoxide and a single remaining particle of sodium metal removed mechanically. The 2-methoxyethyl saccharin-2-acetate (50 g., 0.167 mole) in 70 ml. of warm, dry dimethylsulfoxide was added dropwise over 20 minutes. The reaction mixture was stirred for 1 hour at ambient temperature, quenched into a mixture of concentrated hydrochloric acid (276 ml.) and water (1.84 l.), maintaining the temperature of the quench at 20°–25° C. by an ice-water bath and rate of addition. The slurry was granulated at 6°–8° C. for 1 hour, filtered with cold water wash and dried in air to yield 2-methoxyethyl 4-hydroxy-2H-1,2-benzothiazine-3-carboxylate 1,1-dioxide [32.8 g., 66%; m.p. 120°–122° C.; ir(KBr) 3448, 3226 $cm^{-1}$].

EXAMPLE 5

2-Methoxyethyl 4-Hydroxy-2-methyl-2H-1,2-benzothiazine-3-carboxylate 1,1-Dioxide (I)

2-Methoxyethyl 4-hydroxy-2H-1,2-benzothiazine-3-carboxylate 1,1-dioxide (31.0 g., 0.1035 mole) was combined with 230 ml. of acetone and cooled to 10° C. Methyl iodide (21.9 g., 0.155 mole) was added, followed by the dropwise addition, over 10 minutes, of sodium hydroxide (103.5 ml. of 1 N). The cooling bath was removed and the reaction mixture allowed to slowly warm to room temperature (about 45 minutes), then heated at 35° C. for 2 hours and finally at 39°–40° C. for 16 hours. The reaction mixture was cooled to room temperature, diluted with 200 ml. of acetone, treated with activated carbon, filtered and concentrated in vacuo at 0°–5° C. to about 50 ml. The resulting slurry was filtered, and solids washed with ice-water and then dried in vacuo to yield 2-methoxyethyl 4-hydroxy-2-methyl-2H-1,2-benzothiazine-3-carboxylate 1,1-dioxide [29.26 g., 90%; m.p. 106°–107.5° C.; m/e 313; ir(KBr) 3345, 2941, 1684, 1351, 1053 $cm^{-1}$].

EXAMPLE 6

4-Hydroxy-2-methyl-N-2-pyridyl-2H-1,2-benzothiazine-3-carboxamide 1,1-Dioxide (Piroxicam) (II)

2-Methoxyethyl 4-hydroxy-2H-1,2-benzothiazine-3-carboxylate 1,1-dioxide (28 g., 0.089 mole) and 2-aminopyridine (9.26 g., 0.098 mole) were combined with 500 ml. of xylene in a 1 liter flask equipped with an addition funnel and a reflux, variable take-off distillation head. The stirred reaction mixture was heated to reflux and the xylene distilled at the rate of approximately 100 ml./hour, while maintaining the pot volume almost constant by the addition of fresh xylene. After 6 hours, the head temperature, which had been relatively constant at 134° C., rose to 142° C. and reflux rate slowed. The reaction mixture was then cooled in an ice-bath and the precipitated solids recovered by filtration, with hexane for transfer and wash, and dried at 45° C., in vacuo to yield piroxicam (28.5 g., 96%; m.p. 167°–174° C.). This product was examined by high performance liquid chromatography using 60:40 0.1 M $Na_2HPO_4$ adjusted to pH 7.5 with citric acid:methanol on Micro-Bonda pak $C_{18}$ (Trademark of Waters Associates for a standard hplc column packing consisting of siloxy substituted silica coated on micro-glass beads). Under the conditions employed, piroxicam has a retention time of about 6 minutes, whereas the potential contaminant, $O^4$-methoxyethylpiroxicam, has a retention time of 16.5 minutes. None of the potential contaminant was detected in the product of the present Example.

For purposes of recrystallization, the above piroxicam (25 g.) was taken up in 190 ml. of dimethylacetamide at 70°–75° C., treated with 1.26 g. of activated carbon at 75°–80° C. and filtered through diatomaceous earth with 55 ml. of warm dimethylacetamide for transfer and wash. A mixture of 173 ml. of acetone and 173 ml. of water was cooled to 5°–10° C. The carbon-treated filtrate was added slowly over 10–15 minutes to the chilled aqueous acetone, and the resulting crystals granulated at 0°–5° C. for 5 minutes. Recrystallized piroxicam was recovered by filtration with 154 ml. of cold methanol for transfer and wash. Yield: 18.75 g., 75%; ir(nujol mull) identical with authentic piroxicam.

I claim:

1. A compound of the formula

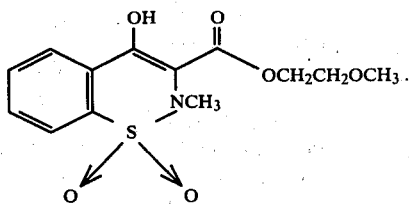

2. A process for converting an ester of the formula

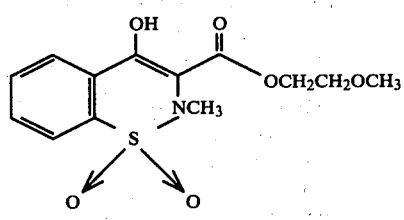

to piroxicam which comprises reacting said ester with 2-aminopyridine in a reaction-inert organic solvent at 115°–175° C. until the reaction is substantially complete.

3. A process of claim 2 wherein the solvent is xylene.

4. A process of claim 2 or 3 wherein byproduct 2-methoxyethanol is removed by codistillation with solvent during the reaction.

* * * * *

UNITED STATES PATENT AND TRADEMARK OFFICE
CERTIFICATE OF CORRECTION

PATENT NO. : 4,289,879
DATED : September 15, 1981
INVENTOR(S) : Joseph G. Lombardino It is certified that error appears in the above-identified patent and that said Letters Patent are hereby corrected as shown below:

Column 6, line 18, delete "4-Hydroxy-2H-1,2-benzothiazine-3-carboxamide", and insert -- 4-Hydroxy-2H-1,2-benzothiazine-3-carboxylate --.

Column 7, lines 3-4, delete "4-hydroxy-2H-1,2-benzothiazine-3-carboxylate", and insert -- 4-hydroxy-2-methyl-2H-1,2-benzothiazine-3-carboxylate --.

Signed and Sealed this

Fifteenth Day of March 1983

[SEAL]

Attest:

Attesting Officer

GERALD J. MOSSINGHOFF

Commissioner of Patents and Trademarks

UNITED STATES PATENT AND TRADEMARK OFFICE
CERTIFICATE OF CORRECTION

PATENT NO. : 4,289,879
DATED : September 15, 1981
INVENTOR(S) : Joseph G. Lombardino It is certified that error appears in the above-identified patent and that said Letters Patent are hereby corrected as shown below:

Column 4, line 47 delete "115-117" and insert --115-175--.

Signed and Sealed this

Twenty-fourth Day of May 1983

[SEAL]

Attest:

DONALD J. QUIGG

Attesting Officer

Acting Commissioner of Patents and Trademarks